US010293276B2

(12) United States Patent
Jones et al.

(10) Patent No.: US 10,293,276 B2
(45) Date of Patent: May 21, 2019

(54) WATER SEPARATION FROM SOLVENT

(71) Applicant: Horizon Technology, Inc., Salem, NH (US)

(72) Inventors: William R. Jones, Northborough, MA (US); David P. Cross, Atkinson, NH (US); Lewis B. Chesno, Brentwood, NH (US)

(73) Assignee: HORIZON TECHNOLOGY, INC., Salem, NH (US)

( * ) Notice: Subject to any disclaimer, the term of this patent is extended or adjusted under 35 U.S.C. 154(b) by 0 days.

(21) Appl. No.: 15/062,611

(22) Filed: Mar. 7, 2016

(65) Prior Publication Data
US 2016/0258850 A1 Sep. 8, 2016

Related U.S. Application Data

(60) Provisional application No. 62/129,605, filed on Mar. 6, 2015.

(51) Int. Cl.
*G01N 1/40* (2006.01)
*B01D 11/04* (2006.01)

(52) U.S. Cl.
CPC ....... *B01D 11/0415* (2013.01); *G01N 1/4005* (2013.01); *G01N 1/4055* (2013.01); *G01N 2001/4061* (2013.01)

(58) Field of Classification Search
CPC .......... G01N 1/40; B01D 11/04; B01D 61/18; B01D 63/06; B01D 63/08; B01D 69/10
USPC ... 210/172.4, 257.2, 321.75, 321.78, 321.84, 210/321.87, 406, 416.1, 444, 460, 497.01, 210/500.27, 500.36, 650, 94, 101, 457, 210/483, 490, 639; 422/534–535; 436/177–178
See application file for complete search history.

(56) References Cited

U.S. PATENT DOCUMENTS

| 2,817,337 | A | * | 12/1957 | Herzig | ....................... | A61J 1/20 215/DIG. 3 |
| 2,878,671 | A | * | 3/1959 | Prosser | .................... | E02D 1/027 222/549 |
| 3,512,940 | A | * | 5/1970 | Shapiro | .................. | B01D 33/01 210/450 |
| 3,687,296 | A | * | 8/1972 | Spinosa | ................. | B01D 33/01 210/406 |

(Continued)

FOREIGN PATENT DOCUMENTS

EP 0660109 6/1995
EP 1588751 10/2005
(Continued)

OTHER PUBLICATIONS

Millipore Immersible Molecular Separators Science 1976, 193, 816.*
(Continued)

*Primary Examiner* — Arlen Soderquist
(74) *Attorney, Agent, or Firm* — Grossman, Tucker, Perreault & Pfleger, PLLC

(57) ABSTRACT

A phase separator and associated method for removal of water from a sample containing analytes in an organic solvent including a vertically extending body portion for vertical extension into a receptacle, the body portion including at least one vertically extending membrane portion on at least one side thereof and a port for introduction of solvent.

1 Claim, 4 Drawing Sheets

(56) References Cited

U.S. PATENT DOCUMENTS

| | | | | |
|---|---|---|---|---|
| 3,862,576 A * | 1/1975 | Pogorski | G01V 5/02 | 436/178 |
| 3,865,548 A * | 2/1975 | Padawer | A61B 5/145 | 356/246 |
| 3,931,428 A * | 1/1976 | Reick | B05D 5/08 | 244/134 B |
| 3,976,572 A * | 8/1976 | Reick | B01D 17/10 | 210/172.1 |
| 4,184,963 A * | 1/1980 | Sternberg | B01D 69/10 | 210/321.87 |
| 4,222,870 A * | 9/1980 | Sternberg | B01D 61/145 | 210/101 |
| 4,391,779 A * | 7/1983 | Miskinis | B01L 3/565 | 215/296 |
| 4,600,507 A * | 7/1986 | Shimizu | G01N 33/491 | 210/321.84 |
| 4,734,196 A * | 3/1988 | Kono | B01D 67/0009 | 210/500.36 |
| 4,759,227 A * | 7/1988 | Timmons | C08J 9/26 | 73/73 |
| 4,778,601 A * | 10/1988 | Lopatin | B01D 67/003 | 210/500.27 |
| 5,010,776 A * | 4/1991 | Lucero | B09B 1/00 | 73/863.23 |
| 5,092,999 A * | 3/1992 | Valenzuela | B01D 29/114 | 210/321.72 |
| 5,215,717 A * | 6/1993 | Conant | B01B 1/00 | 215/276 |
| 5,266,206 A * | 11/1993 | Baker | B01D 17/0208 | 210/259 |
| 5,373,620 A | 12/1994 | Zine | | |
| 5,609,760 A * | 3/1997 | Leach | B01D 17/10 | 210/416.1 |
| 5,733,507 A * | 3/1998 | Zakim | G01N 21/03 | 422/535 |
| 5,755,962 A * | 5/1998 | Gershenson | B01D 25/24 | 210/452 |
| 5,873,980 A * | 2/1999 | Young | B01D 5/0063 | 196/98 |
| 6,103,200 A * | 8/2000 | Babashak | B01L 3/565 | 422/545 |
| 6,172,163 B1 | 1/2001 | Rein et al. | | |
| 6,183,645 B1 * | 2/2001 | DeWitt | B01D 11/04 | 210/321.6 |
| 6,197,260 B1 * | 3/2001 | Bradshaw | B01F 13/002 | 210/295 |
| 6,623,545 B2 | 9/2003 | Thordarson et al. | | |
| 6,749,755 B2 | 6/2004 | Johnson | | |
| 6,755,970 B1 | 6/2004 | Knappe et al. | | |
| 6,780,309 B2 * | 8/2004 | Haldopoulos | A61M 1/0001 | 210/416.1 |
| 6,852,286 B2 * | 2/2005 | Martinez Martinez | B01L 3/508 | 422/501 |
| 7,468,281 B2 * | 12/2008 | Kallury | B01D 61/18 | 210/500.23 |
| 7,520,186 B2 * | 4/2009 | Risk | G01N 1/22 | 73/863.23 |
| 2002/0179529 A1 * | 12/2002 | Johnson | B01D 61/14 | 210/637 |
| 2004/0171169 A1 * | 9/2004 | Kallury | B01D 61/18 | 436/178 |
| 2006/0054556 A1 * | 3/2006 | David | B01D 17/085 | 210/644 |
| 2006/0121269 A1 * | 6/2006 | Miller | B01D 67/0027 | 428/317.9 |
| 2009/0166520 A1 * | 7/2009 | Tuli | G01V 9/00 | 250/253 |
| 2010/0038303 A1 * | 2/2010 | Cai | B01L 3/56 | 210/406 |
| 2013/0228529 A1 * | 9/2013 | Guo | C08K 3/34 | 210/767 |
| 2013/0319958 A1 * | 12/2013 | Cai | B01D 29/085 | 210/808 |
| 2014/0212612 A1 * | 7/2014 | Sbriglia | B29C 67/205 | 428/36.9 |
| 2015/0136681 A1 | 5/2015 | Jordan et al. | | |
| 2015/0375224 A1 * | 12/2015 | Liu | B01L 3/08 | 422/556 |

FOREIGN PATENT DOCUMENTS

| | | |
|---|---|---|
| WO | WO200701667 | 2/2007 |
| WO | WO2013189742 | 12/2013 |

OTHER PUBLICATIONS

International Search Report dated May 31, 2016 issued in related International Patent Application No. PCT/US2016/021158.

* cited by examiner

WATER SEPARATION FROM SOLVENT

CROSS-REFERENCE TO RELATED APPLICATIONS

This application claims the benefit of U.S. Provisional Patent Application Ser. No. 62/129,605, filed on Mar. 6, 2015, which is fully incorporated herein by reference.

FIELD OF THE INVENTION

The present invention relates to the field of chemical laboratory equipment for sample preparation and particularly the use of a hydrophobic membrane of selected geometry to separate water from an organic solvent. A sample extract containing analytes in a solvent for analysis along with water may be passed through the membrane to remove residual water. The analytes may then be isolated for further analytical evaluation.

BACKGROUND

When samples are to be analyzed for organic trace compounds, the samples are typically extracted with an organic solvent. The solvent extracts the compounds from the sample, due to selective chemistry. Before the extract can be analyzed, all residual water should preferably be removed from the extracting solvent. This is due to the adverse effect residual water can have on the analytical instruments that are used to analyze the sample.

U.S. Pat. No. 6,749,755 describes an apparatus and method for separating residual water from a solvent. The device comprises a reservoir containing a solution comprising solvent containing residual water, the reservoir having an opening to allow the solution to drain from the reservoir. A membrane layer is provided comprising a layer of fluoropolymer material, wherein the membrane material has an IPA Bubble Point of greater than or equal to 25 psi. The membrane is positioned in series with the reservoir opening. Vacuum is generated on one side of the membrane layer wherein the solvent containing water passes through the membrane therein removing water from the solvent to provide a solvent with a water level of less than or equal to 1.0 ppm.

SUMMARY

A phase separator for removal of water from a sample containing analytes in an organic solvent comprising a vertically extending body portion for vertical extension into a receptacle, the body portion including at least one vertically extending membrane portion on at least one side thereof and a port for introduction of solvent. The membrane includes a porous hydrophobic material having a porosity of 0.05 microns to 0.20 microns, wherein the body portion has a length of 2.0 to 3.0 inches, a width of 0.25 inches to 0.75 inches and a depth of 0.40 to 0.60 inches.

The present disclosure also relates to a method for removing water from an organic solvent comprising supplying a phase separator including a vertically extending body portion for vertical extension into a receptacle, the body portion including at least one vertically extending membrane portion on at least one side thereof and a port for introduction of solvent. The phase separator is then positioned in a receptacle followed by introduction into the phase separator an organic solvent solution containing analytes and water and introducing a vacuum wherein one of the following two conditions are achieved: (1) when the organic solvent (e.g. hexane) is relatively less dense than said water, the water is positioned on the bottom of said organic solvent within the phase separator and the vacuum pulls the solvent through the membrane leaving said water behind; or (2) when the organic solvent (e.g. methylene chloride) is relatively more dense than the water, the water is positioned on the top of the organic solvent within the phase separator and the vacuum pulls the solvent through the membrane leaving water behind.

DETAILED DESCRIPTION

Figure 1:
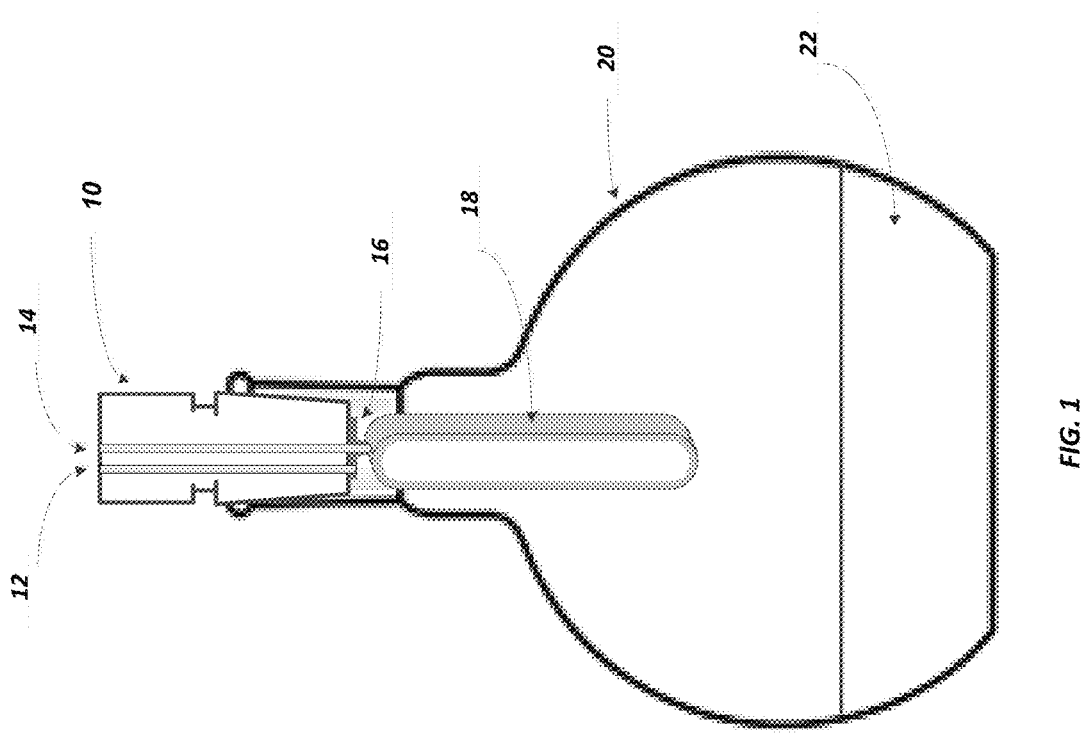
FIG. 1 is a perspective view of the apparatus of the present disclosure which illustrates the phase separator device body sized to fit within a flask.

FIG. 1 illustrates one configuration of the present disclosure. More specifically, as shown therein, a 24/40 adaptor is shown at 10, preferably made of fluoropolymer such as polytetrafluoroethylene. At 12 one can then supply a vacuum port and at 14 one can supply the extract solvent port. At 16 can be seen a male Luer adaptor with vacuum port. The phase separator is shown at 18, the flask at 20, and the extracted solvent at 22. The flask may preferably be a 250 ml flask, with a flat bottom portion.

Figure 2:
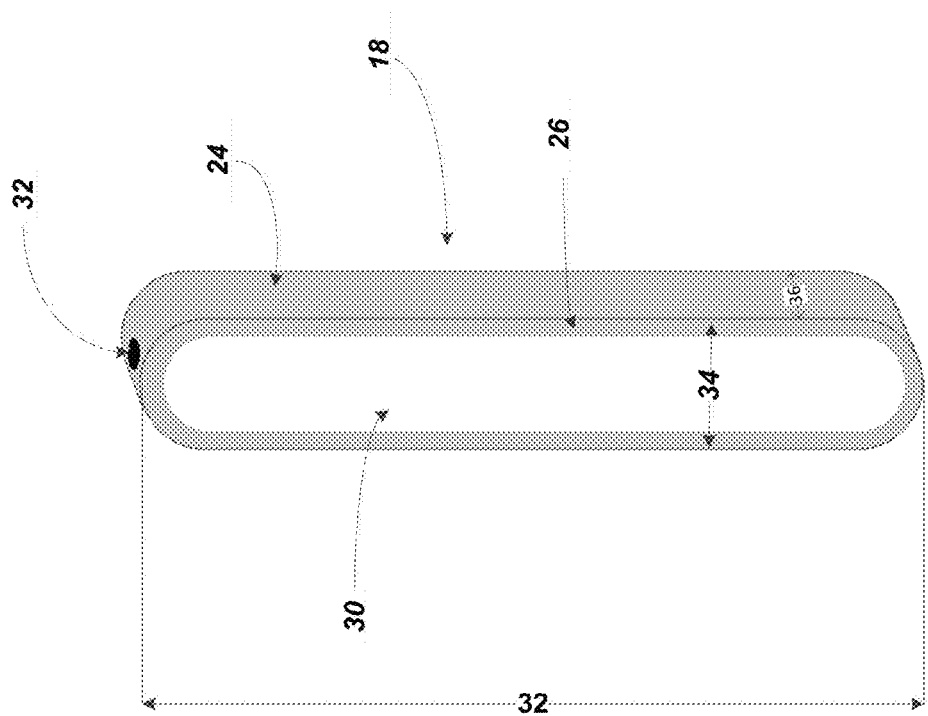
FIG. 2 is a more detailed view of the phase separator device.

FIG. 2 provides an expanded view of the phase separator 18. As illustrated, the phase separator contains a body portion 24 that is preferably sized to retain up to 5.0 ml of water from any given extract. The body portion may comprise a polyolefin polymer, such as polyethylene. More preferably, the body portion may comprise ultrahigh molecular weight polyethylene, which is reference to a polyethylene having a weight average molecular weight (Mw) of between 2,000,000 and 6,000,000. The body portion 24 may also be manufactured from polypropylene type polymer material or high density polyethylene (HDPE) at a density of greater than 0.94 g/cc, or in the range of 0.94-0.96 g/cc.

A membrane is shown at 30, which membrane is also preferably selected from a polyolefin polymer material. More preferably, the polyolefin polymer material is an ultrahigh molecular polyethylene (UHMWPE) which is again reference to a polyethylene having a weight average molecular weight (Mw) of between 2,000,000 and 6,000,000.

One particularly preferred example for the body portion is the material sold under the name PLASLUBE™ PE 4000 LE from TechmerES that has a specific gravity of 0.943, a melt flow rate of 4.0 g/10 minute, tensile strength of 4700 psi, tensile elongation at break of 80%, flexural modulus of 130,000 psi and flexural strength of 7000 psi. It also has a HDT at 66 psi (unannealed) of 200° F.

Another particularly preferred example for the body portion is the material sold under the name MARLEX® HXM 50100 from Chevron Phillips Chemical Company LP. HXM 50100 is a high molecular weight high density polyethylene (hexane) copolymer. HXM 50100 has a specific gravity of 0.948, a melt flow rate of 10.0 g/10 minute, tensile strength of 3600 psi, tensile elongation at break of 700% and flexural modulus of 175,000 psi. It also has a HDT at 66 psi (unannealed) of 173° F.

The polyolefin polymer used for the membrane 30 as described above, will preferably have a pore size in the range of 0.05 microns to 0.2 microns. More preferably, the pore size will be in the range of 0.10 microns to 0.20 microns, and in a most preferred configuration, the pore size will be 0.15 microns. The membrane 30 will also preferably have a thickness in the range of 20 microns to 120 microns, more preferably, 50 microns to 100 microns, and even more preferably, 75 microns to 100 microns. One particular preferred thickness is 95 microns. The membrane 30 has an air permeability, which is best characterized by a Gurly number of 18 s for 50 mL. The membrane also may have an IPA Bubble Point of 20-35 psi. One particularly preferred membrane in such range has an IPA Bubble Point of 22.19 psi. Another particularly preferred membrane in such range has a IPA Bubble Point of 32.05 psi.

One particular example of a membrane 30 as described above is known as a SOLUPOR® membrane, designated Y083G-14P02E, from Lydall Performance Materials. SOLUPOR® membranes are highly porous with high gas, air and liquid permeability. Combined with a controlled pore size, this makes SOLUPOR® membranes suitable for a range of filtration applications. SOLUPOR® membranes Y083G-14P02E is made from UHMWPE and has a total weight per surface area of 14 g/m$^2$, a thickness of 95 μm, a porosity of 85%, an air permeability (Gurley number) of 18 s/50 mL and a mean flow pore size of 0.15 μm.

As shown by arrow 32, the phase separator 18 has a vertically extending length dimension, which preferably falls in the range of 2.0 to 3.0 inches. The width dimension as illustrated by arrow 34 is preferably in the range of 0.25 inches to 0.75 inches. The depth of the phase separator as shown by arrow 36 is preferably in the range of 0.40 inches to 0.60 inches. The wall thickness shown at 26 will preferably be 0.05 inches to 0.10 inches, more preferably 0.07 inches to 0.10 inches, and in particular, a wall thickness of 0.08 inches is employed. In addition, the diameter of the preferred Luer port illustrated at 32 is preferably 0.10 to 0.20 inches, more preferably 0.15 to 0.20 inches, and a particularly preferred diameter of the Luer port is 0.16 inches. Other ports may be such that they involve a press fit, compression fit, or National Pipe Thread Taper (NPT) fitting.

It should be appreciated from the above, that the dimensions of the phase separator 18 herein are such that an optimum surface area of membrane 30 can now be provided within a typical laboratory flask or even a given laboratory separatory funnel with a 24/40 tapered neck.

Figure 3:
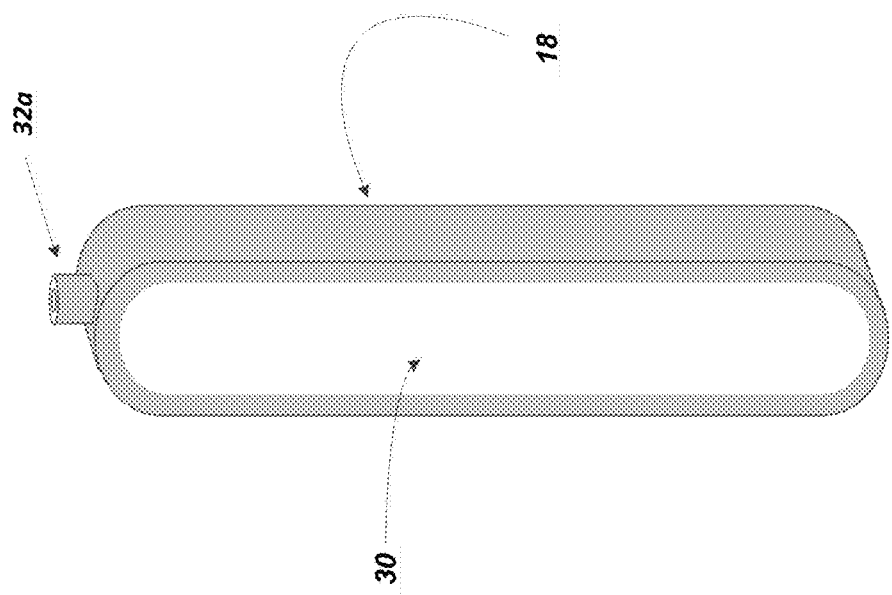
FIG. 3 is a view of a phase separator device including membrane portions on both sides of the body portion.

It is worth noting that as shown in FIG. 2, the phase separator 18 has membrane 30 on one side of the body portion 24. It is contemplated herein, and as shown in FIG. 3, that the phase separator may also have a similar membrane on the back portion (i.e. on the wall portion opposite membrane 30). This would then double the available surface area of the membrane for transport of non-polar solvents. As also illustrated in FIG. 3, one may optionally include an extension 32a to the Luer port 32 which can improve sealing to the male Luer.

The membrane 30 is preferably bonded to the wall portion 26 of the body portion 24 by thermal bonding. More specifically, the surface temperature of the wall portion, in the case of UHMWPE resin, is preferably heated to a temperature of 270° F. to 305° F. The membrane 30, in the case of a such resin, is pressed against the wall portion 26 for 5.0 seconds, at a pressure of 10 psig to 30 psig. A thermal bond is then formed that is adequate for use herein. One may also apply the membrane to the body and then apply heat and pressure on the membrane side to the UHMWPE resin body.

As may now be appreciated with reference to FIG. 1, upon application of a vacuum through vacuum port 12, liquid introduced at port 14 will flow into the phase separator 18 and organic solvents will then pass through the membrane 30 leaving water behind to collect in the body portion 24. It is contemplated that the device may operate up to --25 inches Hg or at 12.25 psig. Accordingly, by pulling a vacuum as indicated, solvent with dissolved analytes along with residual water will be pulled into the phase separator 18 and as the phase separator is in a vertical orientation, when solvent is relatively less dense than water (e.g. hexane), the vacuum can pull the hexane off of the top of the water and through the membrane 30. If a relatively more dense solvent than water is present (e.g. methylene chloride), the solvent may be pulled through the bottom of the membrane 30, and water is still left behind.

Reference to vertical orientation may be understood as arranging the phase separator as relatively perpendicular to the flask, or it may also be at an angle of +/−45 degrees to vertical, and still provide the beneficial separation discussed above.

It may be appreciated that the foregoing structure may provide a phase separator 18 which can easily fit into flask 20, and which has sufficient capacity to hold at least 5 mL of sequestered water from the extract. Furthermore, the phase separator 18 is short enough to allow easy removal of the flask 20 from the phase separator 18 when installed in a system, as well as short enough to avoid immersion of the phase separator 18 in the collected processed extract.

By way of example, the device illustrated in FIGS. 1-3 can operate such that analytes are isolated from a solvent extract for further analytical evaluation. For example, the device herein is particularly useful for conducting EPA Method 1664, Revision B. Accordingly, one may start with a sample of analytes of non-volatile hydrocarbons, vegetable oils, animal fats, waxes, soaps, and greases that is initially found in an aqueous matrix of surface water, saline water, industrial aqueous waste or domestic aqueous waste. This combination of analytes in the identified aqueous matrix is first introduced through a solid phase extraction disk which broadly isolates the analytes from the aqueous phase. See FIG. 4 which shows the placement of the solid phase extraction disk holder 36 and solid phase extraction disk 38. After this step, the analytes on the surface of the extraction disk are then exposed to organic solvents, the analytes are then dissolved and now introduced into the device shown in FIG. 1. At that point, any residual water in the solvent is removed by passing the solvent through membrane and the water is left behind. As noted above, when the solvent is more dense than water, as in the case of methylene chloride, the solvent towards the bottom of the phase separator will pass through the membrane and the water is captured in the interior of the phase separator 18.

Figure 4:
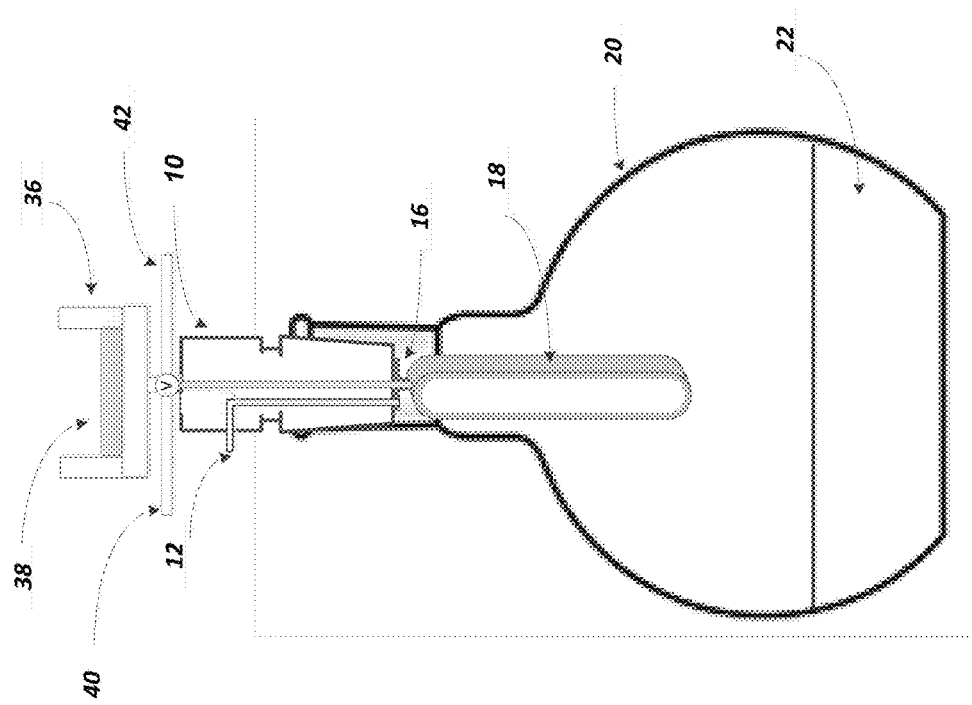
FIG. 4 is a view of the phase separate device including a solid phase extraction disk.

In addition, as can also be seen in FIG. 4, there is a valve "V" which is connected to port lines 40 and 42. The purpose of the valve is to: (1) direct solvents that precondition and clean the SPE disk to solvent waste (arbitrarily to the right of the valve), or direct sample water to water waste (arbitrarily going to the left) or Direct solvent extract to the phase separator/flask below.

Similar methods have been found suitable for application of EPA method 8081, which is targeted from the ultimate analysis of organochlorine pesticides by gas chromatography. Similar to the above, the organochlorine pesticides may be captured on a solid phase extraction disk and then exposed to a hexane solvent, passed through the device illustrated in FIG. 1, and the solvent containing the organochlorine pesticides is isolated with the water removed. The solvent containing the organochlorine pesticides may then be reduced in volume to a level of 0.5 ml to 5 ml for GC analysis.

In addition, the device herein may be used for EPA method 8082 to isolate and analyze polychlorinated biphenyls (PCBs) by gas chromatography. Similarly, the PCBs may be collected from a given sample matrix medium on a solid phase extraction disk to isolate the PCBs from an aqueous medium, followed by exposure to organic solvent in which they dissolve and are then allowed to pass through the device shown in FIG. 1. The solvent passes through the membrane 30, water is left behind, and the solvent may then be concentrated for GC evaluation.

Furthermore, the device herein may be used for removing water from organic solvent extracts using solid phase extraction for the analysis of semivolatile organic compounds listed in EPA methods 525.2, 525.3 and 8270D.

What is claimed is:

1. A method for removing water from an organic solvent comprising:
    supplying a phase separator including a vertically extending body portion for vertical extension through a tapered neck of at least a 24/40 size of a receptacle, said body portion including at least one vertically extending membrane portion on at least one side thereof and a port for introduction of solvent;
    said membrane portion comprising porous hydrophobic material having a porosity of 0.05 microns to 0.20 microns, said body portion having a length of 2.0 to 3.0 inches, a width of 0.25 inches to 0.75 inches, and a depth of 0.40 to 0.60 inches;
    supplying an adaptor having a port for vacuum and a port for passage of solvent, wherein said phase separator is attached to said adaptor at said port for passage of solvent, and wherein said adaptor includes a tapered neck sized to be received into said tapered neck of at least 24/40 size of said receptacle, wherein said phase separator is attached to said adaptor at said port for passage of solvent such that said port for introduction of solvent of said phase separator is in fluid communication with said port for passage of solvent of said adaptor and arranged downstream of said port for passage of solvent of said adaptor, and said membrane is arranged downstream of said port for introduction of solvent of said phase separator;
    extending said phase separator through said tapered neck of at least 24/40 size of said receptacle;
    positioning said adaptor into said tapered neck of at least 24/40 size of said receptacle and said phase separator vertically beneath said adaptor inside said receptacle;
    introducing into said phase separator an organic solvent solution containing analytes and water and introducing a vacuum wherein one of the following two conditions are achieved:
        (i) when said organic solvent is relatively less dense than said water, said water is positioned on the bottom of said organic solvent within said phase separator and said vacuum pulls said solvent through said membrane leaving said water behind; or
        (ii) when said organic solvent is relatively more dense than said water, said water is positioned on the top of said organic solvent within said phase separator and said vacuum pulls said solvent through said membrane leaving water behind.

* * * * *